United States Patent [19]

Kimura et al.

[11] Patent Number: 5,505,770
[45] Date of Patent: Apr. 9, 1996

[54] ANTIFOULING AGENT

[75] Inventors: Ryoji Kimura; Mitsuhiro Hamajima, both of Saitama, Japan

[73] Assignee: Asahi Denka Kogyo Kabushiki Kaisha, Tokyo, Japan

[21] Appl. No.: 232,091

[22] PCT Filed: Feb. 8, 1993

[86] PCT No.: PCT/JP93/00161
§ 371 Date: Apr. 29, 1994
§ 102(e) Date: Apr. 29, 1994

[30] Foreign Application Priority Data

Aug. 12, 1991 [JP] Japan ................... 3-202026

[51] Int. Cl.$^6$ .................. A01N 57/14; A01N 31/08
[52] U.S. Cl. .................. 106/18.31; 106/18.35; 424/78.09; 514/142; 514/143; 514/147
[58] Field of Search .............. 106/15.05, 18.31, 106/18.35; 424/78.09; 514/142, 143, 147

[56] References Cited

U.S. PATENT DOCUMENTS 3,966,677  6/1976  Sonoyama et al. ............ 524/141
4,104,259  8/1978  Kato et al. ............ 524/117

FOREIGN PATENT DOCUMENTS 48-43618  12/1973  Japan .
3-128302  5/1991  Japan .

*Primary Examiner*—Anthony Green
*Attorney, Agent, or Firm*—Young & Thompson

[57] ABSTRACT

An antifouling agent characterized by containing one or more compounds represented by the following general formula (I) as an active ingredient:

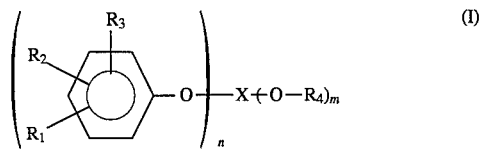

(wherein $R_1$, $R_2$ and $R_3$ independently represent each a hydrogen atom, a halogen atom or an alkyl group carrying 1 to 30 carbon atoms; X represents an inorganic oxygen acid residue; n is from 1 to 4; m is from 0 to 3; and $R_4$ represents a hydrogen atom or an alkyl or alkenyl group carrying 1 to 30 carbon atoms and optionally having an ether bond.)

5 Claims, No Drawings

ANTIFOULING AGENT

TECHNICAL FIELD

This invention relates to an antifouling agent which aims at preventing damages due to the adhesion and propagation of aquatic pests in sea water or industrial water systems. More particularly, it relates to an antifouling agent which is to be used for protecting submerged structures such as ships, fishing nets, buoys or sea water induction pipes from the adhesion of aquatic pests to the surface thereof.

BACKGROUND ART

Submerged structures, for example, ships, port facilities, buoys, pipe lines, bridges, excavators for seabed oil fields, water pipes in electric power plants or seaside plants, fish nets or fish breeding rafts suffer from the adhesion of large-sized animals and plants such as barnacle, hard-shelled mussel and laver and small-sized ones such as diatom and bacteria, which causes various damages, for example, corrosion of the structures, an increase in sea water friction of ships, death of a number of fishes due to fishing net jamming, settling out due to gain in weight and a decrease in operating efficiency. Further, in industrial water systems with the use of natural water such as river water and lake water as, for example, cooling water or in circulating cooling systems with the use of moderately or highly purified city water, the abnormal propagation of, for example, bacteria, diatom, blue-green algae and spirogyra causes various troubles including deterioration of water qualities, a decrease in cooling efficiency and pipe jamming due to the adhesion thereof to the walls of instruments and reduction in flow rate.

In order to prevent these troubles caused by aquatic pests, there have been employed antifouling agents containing inorganic heavy metal compounds such as copper suboxide, copper rhodanide and mercury oxide or organic metal compounds such as tributyltin oxide, triphenyltin oxide and tributyltin (meth)acrylate polymers.

However, these compounds which have been conventionally employed for the above-mentioned purpose are not only highly toxic ones and thus should be handled with religious care but also result in some problems including deformation of fishes due to the accumulation thereof in fish bodies and environmental pollution. Therefore it has been urgently required to use an antifouling agent free from any heavy metals or organic metals.

As such an antifouling agent free from any heavy metals or organic metals, Japanese Patent Laid-Open No. 128302/1991 has proposed the use of alkylphenols. However, these alkyl-phenols are not usable in practice at present, since the effects thereof are lost within only a short period of time.

Accordingly, it is an object of the present invention to provide an antifouling agent scarcely causing any problems in hygienic safety and the environment (namely, having a low toxicity and a low persistence) and being capable of exerting its effects over a long period of time without adversely affecting the ecosystem or the working environment.

DISCLOSURE OF THE INVENTION

In order to achieve the above-mentioned object, the present inventors have conducted extensive studies. As a result, they have found out that the above object can be achieved by using an inorganic oxygen acid ester compound of a specific phenol.

Accordingly, the present invention provides an antifouling agent characterized by containing one or more compounds represented by the following general formula (I) as an active ingredient.

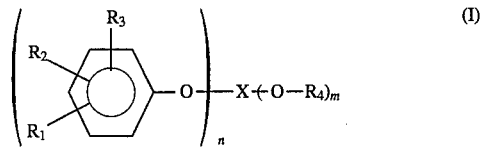

(wherein $R_1$, $R_2$ and $R_3$ independently represent each a hydrogen atom, a halogen atom or an alkyl group carrying 1 to 30 carbon atoms; X represents an inorganic oxygen acid residue; n is from 1 to 4; m is from 0 to 3; and $R_4$ represents a hydrogen atom or an alkyl or alkenyl group carrying 1 to 30 carbon atoms and optionally having an ether bond.)

DETAILED DESCRIPTION OF THE INVENTION

Now, the present invention, the gist of which has been described above, will be illustrated in greater detail.

Regarding the groups $R_1$, $R_2$ and $R_3$ in the compound represented by the above general formula (I), examples of the halogen atom include chlorine, bromine, fluorine and iodine atoms and examples of the alkyl groups carrying 1 to 30 carbon atoms include linear and branched alkyl groups such as methyl, ethyl, propyl, isopropyl, butyl, isobutyl, sec-butyl, tert-butyl, amyl, hexyl, heptyl, octyl, isooctyl, 2-ethylhexyl, tert-octyl, nonyl, isononyl, tert-nonyl, decyl, isodecyl, dodecyl, tridecyl, isotridecyl, tetradecyl, hexadecyl, octadecyl, eicosyl, docosyl, tetracosyl and triacontyl groups.

The inorganic oxygen acid residue represented by X means those obtained by eliminating a hydroxyl group from an inorganic oxygen acid. Examples thereof include residues derived from phosphorous acid, phosphoric acid, pyrophosphoric acid, silicic acid, orthosilicic acid, boric acid, carbonic acid, aluminic acid, titanic acid, selenic acid, stannic acid, molybdic acid, tungstic acid and zirconic acid. Thus, for residues derived from phosphorous acid and phosphoric acid, it will be recognized that the value of X in general formula I will be P and P=O, respectively.

As examples of the alkyl or alkenyl group carrying 1 to 30 carbon atoms and optionally having an ether bond which is represented by $R^4$, allyl, oleyl, methoxyethyl, ethoxyethyl, butoxyethyl, phenoxyethyl, butoxyethoxyethyl and phenoxypolyethoxyethyl groups may be cited, in addition to the alkyl groups as cited above.

Therefore, examples of the inorganic oxygen acid ester compound of phenol represented by the above general formula (I) which is to be used in the present invention include phosphite compounds such as triphenyl phosphite, tris(4-chlorophenyl) phosphite, tris(2,4-di-tert-butylphenyl) phosphite, tris(2,4-di-tert-butyl- 5-methylphenyl) phosphite, tris(octylphenyl) phosphite, tris(nonylphenyl) phosphite, tris(mono- and dinonylphenyl) phosphite, tris(dodecylphenyl) phosphite, octyl diphenyl phosphite, bis(2,4-di-tert-butylphenyl) acid phosphite, bis(nonylphenyl) acid phosphite, dioctyl nonylphenyl phosphite and mono(nonylphenyl) acid phosphite; phosphate compounds such as triphenyl phosphate, tris(2,4,6-tribromophenyl) phosphate, tricresyl phosphate, trixylyl phosphate, tris(ethylphenyl) phosphate, tris(isopropylphenyl) phosphate, tris-(mono- and diisopropylphenyl) phosphate, tris(4-tert-butylphenyl) phosphate, tris(nonylphenyl) phosphate, bis(4-tert-butylphenyl) phosphate, bis(nonylphenyl) phenyl phosphate, diphenyl octyl phosphate and bis(nonylphenyl) butoxyethyl phosphate; pyrophosphate compounds such as bis(nonylphenyl) pyrophosphate; borate compounds such as triphenyl borate and tris(nonylphenyl) borate; silicate compounds such as bis(nonylphenyl) silicate and bis(dodecylphenyl) silicate; orthosilicate compounds such as tetra(nonylphenyl) orthosilicate and bis(nonylphenyl) dimethyl orthosilicate; carbonate compounds such as diphenyl carbonate and bis(nonylphenyl) carbonate; titanate compounds such as tetra(nonylphenyl) titanate; zirconate compounds such as tetra(nonylphenyl) zirconate; and aluminate compounds such as tris(nonylphenyl) aluminate. In the above-mentioned phosphate and phosphite compounds, being derived from the trivalent acids phosphoric acid and phosphorous acid, respectively, it will be recognized that n+m=3, in the above general formula I.

Among these compounds represented by the general formula (I), those wherein X is a residue derived from an oxygen acid of phosphorus are particularly preferable, since they are not only highly effective as an antifouling agent but also have a low toxicity and scarcely cause environmental pollution.

Among the above-mentioned compounds wherein X is a residue derived from an oxygen acid of phosphorus, those wherein at least one of $R_1$, $R_2$ and $R_3$ is an alkyl group carrying 3 to 12 carbon atoms are preferable, since they exhibit excellent effects. Among these compounds, tris(alkylphenyl) phosphites and tris(alkylphenyl) phosphates may be cited as preferable ones.

The present invention relates to an antifouling agent containing one or more compounds represented by the above general formula (I) as an active ingredient. The antifouling agent can be used combinedly with one or more conventional antifouling agents and thus the effects can be sustained for a prolonged period of time in some cases.

Examples of the antifouling agents which can be used together with the compound represented by the general formula (I) to be used in the present invention include thiuram compounds such as tetramethylthiuram disulfide, tetraethylthiuram disulfide, tetra-n-propylthiuram disulfide, tetraisopropylthiuram disulfide, tetra-n-butylthiuram disulfide, tetraisobutylthiuram disulfide, N,N'-ethylenebisthiocarbamoyl sulfide, N,N'-propylenebisthiocarbamoyl sulfide and N,N'-butylenebisthiocarbamoyl sulfide; copper-based metal powders such as copper powder and copper/nickel alloy powder; copper compounds such as cuprous oxide, cuprous thiocyanate, basic copper carbonate, copper pyrophosphate, copper naphthenate, copper abietate and copper oxyquinoline; dithiocarbamate compounds such as zinc dimethyldithiocarbamate, zinc diethyldithiocarbamate, zinc dibutyldithiocarbamate, zinc ethylphenyldithiocarbamate, zinc ethylenebisdithiocarbamate, zinc propylenebisdithiocarbamate, zinc bis(dimethyidithiocarbamoyl)ethylenebisdithiocarbamate, manganese ethylenebisdithiocarbamate, nickel dimethyldithiocarbamate, nickel dibutyldithiocarbamate, copper dimethyldithiocarbamate and iron dimethyldithiocarbamate; benzimidazole compounds such as 2-(4-thiazolyl)benzimidazole, methyl- 1-(ω-cyanopentylcarbamoyl)-2-benzimidazole, zinc 2-mercaptobenzimidazole and 2-thiocyanomethylthiobenzimidazole; benzothiazole compounds such as 2-mercaptobenzothiazole, 2-(thiocyanomethylthio)benzothiazole, 2-(thiocyanomethylsulfonyl)benzothiazole, 2-thiocyanoethylthio-4-chlorobenzothiazole, 2-thiocyanopropylthio-5,7-dichlorobenzothiazole and 2-thiocyanomethylthio-4,5,6,7-tetrachlorobenzothiazole; nitrile compounds such as tetrachloroisophthalonitrile and 5-chloro-2,4-difluoro-6-methoxyisophthalonitrile; isothiazoline compounds such as 4,5-dichloro-2-n-octyl-4-isothiazolin-3-one, 2-n-octyl-4-isothiazolin-3-one and 1,2-benzoisothiazolin-3-one; triazol compounds such as 1-[2-(2,4-dichlorophenyl)-4-propyl-1,3-dioxolanyl-2-methyl]-1H-1,2,4-triazole and 4,4-dimethyl-2-(1,2,4-triazol-1-yl)-1-(4-trifluoromethyl-2-chlorophenyl)-1-penten-2-ol; pyridine compounds such as 2,3,5,6-tetrachloro-4-(methylsulfonyl)pyridine, 2,3,6-trichloro-4-propylsulfonylpyridine and 2,6-dichloro-3,5-dicyano-4-phenylpyridine; triazine compounds such as 2,4-dichloro-6-(a-chloroanilino)-s-triazine, 2-chloro-4-methylamino-6-isopropylamino-s-triazine, 2-chloro-4,6-bis(ethylamino)-s-triazine, 2-chloro-4,6-bis (isopropylamino)-s-triazine, 2-methylthio-4,6-bis (ethylamino)-s-briazine, 2-methylthio-4-ethylamino-6-isopropylamino-s-triazine and 2-methylthio-4-t-butylamino- 6-cyclopropylamino-s-triazine; urea compounds such as 3-(3,4-dichlorophenyl)-1,1-dimethylurea, 3-(3,4-dichlorophenyl)-1-methoxy-1-methylurea, 1-(α, α'-dimethylbenzyl)-3-methyl-3-phenylurea and 1-(2-methylcyclophenyl)-3-phenylurea; quinone compounds such as 2-amino-3-chloro-1,4-naphthoquinone and 2,3-dicyano-1,4-dithiaanthraquinone; N-haloalkylthio compounds such as N-trichloromethylthiotetrahydrophthalimide, N-1,1,2,2-tetrachloroethylthiotetrahydrophthalimide, N-trichloromethylthiophthalimide, N-fluorodichloromethylthiophthalimide, N,N-dimethyl-N'-phenyl-N'-(fluorodichloromethylthio)sulfurylamide, trichloromethylthiomethanesulfon-p-chloroanilide, N-(1,1, 2,2-tetrachloro-2-fluoroethylthio)methanesulfonanilide, N-fluorodichloromethylthio-N- 3-chlorophenyl-N'-dimethylurea, N-fluorodichloromethylthio-N-3,4-dichlorophenyl-N'-methylurea and N-fluorodichloromethylthio-N-trissulfonyl-N-methylamine; maleimide compounds such as N-(2-chlorophenyl)maleimide, N-(4-fluorophenyl)maleimide, N-(3,5-dichlorophenyl)maleimide, N-(2,4,6-trichlorophenyl)maleimide, N-4-tolylmaleimide and N-2,4-xylylmaleimide; thiadiazine compounds such as 3,5-dimethyltetrahydro-1,3,5,2(H)-thiadiazin-2-one, 3,3'-ethylenebis(tetrahydro- 4,6-dimethyl-2H-1,3,5-thiadiazin-2-one, 3,5-dimethyl-2-thiotetrahydro-1,3,5-thiadiazine and 3,5-dibenzyltetrahydro-1,3,5-thiadiazin-2-thione; thiocyanogene compounds such as methyl thiocyanide, chloromethyl thiocyanide, ethyl thiocyanide, methylenebisthiocyanate, chloromethylenebisthiocyanate, ethylenebisthiocyanate, chloroethylenebisthiocyanate, isobornyl thiocyanacetate, methyl isothiocyanate, allyl isothiocyanate, phenyl isothiocyanate and benzyl isothiocyanate; and alkylphenol compounds such as caprylphenol and nonylphenol.

The inorganic acid ester compound of phenol represented by the above general formula (I) to be used in the present invention can be formulated into a solution of a high concentration of, for example, about 80% by weight by which fishing nets, etc., are coated by immersing therein. Alternately, it may be added to a coating and applied to ships or submerged structures as an antifouling coating. The content of the inorganic acid ester compound of phenol in these coating compositions or antifouling solutions for fishing nets is appropriately selected preferably within a range of from 0.5 to 90% by weight, still preferably from 5 to 80% by weight, by taking, for example, the purpose of the application and the fouling period into consideration.

Components usable in the preparation of the above-mentioned coatings or antifouling solutions are not particularly restricted but those which have been conventionally employed for preparing these coatings and antifouling solutions may be used as such.

As resin vehicles to be used in organic solvent-based coatings, for example, vinyl chloride-based resins, chlorinated rubber-based resins, chlorinated polyethylene resins, chlorinated polypropylene resins, acrylic resins, styrene-butadiene resins, polyester-based resins, epoxy resins, polyamide resins, petroleum resins, silicone resins, silicone rubber-based resins, wax, paraffin, rosin esters and rosin-based resins may be used either singly or combinedly. As resin vehicles to be used as water-based coatings, acrylic emulsion resins, epoxy emulsion resins and vinyl acetate resins are usable.

Further, publicly known antifouling agents may be used as an antifouling aid together with the inorganic ester compound of phenol of the present invention. In addition, plasticizers, coloring pigments, fillers and solvents, which have been commonly employed in the art, may be blended therewith at an arbitrary ratio.

To further illustrate the present invention in greater detail, the following Examples will be given. However it is to be understood that the present invention is not restricted thereto.

EXAMPLE 1

To 100 parts by weight of a 30% xylene solution of chlorinated rubber containing 65% of chlorine was added 50 parts by weight of a sample compound. After thoroughly stirring, the mixture was applied onto a hard vinyl chloride board and dried for 24 hours to thereby give a test piece.

In Yokosuka, Kanagawa, this test piece was placed on a test raft and immersed in sea water in a depth of 1 m. Then the degree of fouling due to the adhesion of organisms was observed with the lapse of time and the ratio of the adhesion area per unit coated area was measured.

The results were evaluated in four grades in accordance with the following criteria. Table 1 summarizes the results.

A: no adhesion was observed.

B: adhesion was observed in an area of 50% or less.

C: adhesion was observed in an area exceeding 50%.

D: adhesion was observed over the whole surface and the coated surface was completely covered.

TABLE 1

| No. | Sample compound | After 1 month | After 3 months | After 6 months | After 12 months |
|---|---|---|---|---|---|
| Ex. | | | | | |
| 1-1 | tris(nonylphenyl) phosphite | A | A | A | A |
| 1-2 | bis(nonylphenyl) acid phosphite | A | A | A | A |
| 1-3 | tris(isopropylphenyl) phosphate tris(nonylphenyl) phosphite (1:1) | A | A | A | A |
| 1-4 | tris(nonylphenyl) borate | A | A | A | B |
| 1-5 | tris(octylphenyl) phosphite | A | A | A | A |
| 1-6 | bis(mono- and dinonylphenyl) phosphite | A | A | A | A |
| 1-7 | bis(octylphenyl) pyrophosphate | A | A | A | A |
| 1-8 | tetrakis(nonylphenyl) silicate | A | A | A | B |

TABLE 1-continued

| No. | Sample compound | After 1 month | After 3 months | After 6 months | After 12 months |
|---|---|---|---|---|---|
| Comp. Ex. | | | | | |
| 1-1 | none | B | D | D | D |
| 1-2 | copper suboxide | A | B | C | D |
| 1-3 | nonylphenol | A | C | D | D |

EXAMPLE 2

To 100 parts by weight of a 30% xylene solution of a vinyl chloride/vinyl acetate copolymer resin was added 20 parts by weight of a sample compound. After thoroughly stirring, the mixture was applied onto a hard vinyl chloride board and dried for 24 hours to thereby give a test piece. By using this test piece, the fouling conditions due to the adhesion of organisms were examined in the same manner as the one described in Example 1.

Table 2 summarizes the results.

TABLE 2

| No. | Sample compound | After 1 month | After 3 months | After 6 months | After 12 months |
|---|---|---|---|---|---|
| Ex. | | | | | |
| 2-1 | tris(octylphenyl) phosphite | A | A | A | A |
| 2-2 | tris(nonylphenyl) phosphite | A | A | A | A |
| 2-3 | tris(mono- and dinonylphenyl) phosphite | A | A | A | A |
| 2-4 | bis(nonylphenyl) acid phosphite | A | A | A | A |
| 2-5 | tris(isopropylphenyl) phosphate tris(nonylphenyl) phosphite (1:1) | A | A | A | A |
| 2-6 | tris(nonylphenyl) borate | A | A | A | B |
| 2-7 | bis(octylphenyl) pyrophosphate | A | A | A | A |
| 2-8 | tetrakis(nonylphenyl) silicate | A | A | A | B |
| Comp. Ex. | | | | | |
| 2-1 | none | B | D | D | D |
| 2-2 | copper suboxide | A | C | D | D |
| 2-3 | nonylphenol | A | B | D | D |

EXAMPLE 3

30 parts by weight of each sample compound as listed in Table 3 was added to 100 parts by weight of xylene and thoroughly mixed in a high-speed homomixer to thereby give an antifouling agent for fishing net.

A test net (knot-free, 60 strand-twisted, 20 cm× 30 cm) was dyed by immersing with the use of this antifouling agent for fishing net. After air-drying for 2 days, the degree of fouling due to the adhesion of organisms was examined. Table 3 summarizes the results.

TABLE 3

| No. | Sample compound | After 1 month | After 3 months | After 6 months | After 12 months |
| --- | --- | --- | --- | --- | --- |
| Ex. | | | | | |
| 3-1 | tris(nonylphenyl) phosphite | A | A | A | A |
| 3-2 | tris(nonylphenyl) phosphate | A | A | A | A |
| 3-3 | bis(nonylphenyl) butoxyethoxyethyl phosphate | A | A | A | A |
| 3-4 | bis(nonylphenyl) acid phosphite | A | A | A | A |
| 3-5 | tris(isopropylphenyl) phosphate tris(nonylphenyl) phosphite (1:1) | A | A | A | A |
| 3-6 | tris(nonylphenyl) borate | A | A | A | B |
| 3-7 | bis(octylphenyl) pyrophosphate | A | A | A | A |
| 3-8 | tetrakis(nonylphenyl) silicate | A | A | A | B |
| Comp. Ex. | | | | | |
| 3-1 | none | B | D | D | D |
| 3-2 | nonylphenol | A | B | D | D |

As the results of these Examples clearly show, the effects of alkylphenol compounds used as an antifouling agent for controlling aquatic pests are lost within a short period of time, while the effects of the specific inorganic oxygen acid ester compounds of phenol according to the present invention are sustained for a prolonged period of time.

Further, it is believed that the inorganic oxygen acid ester compounds of phenol of the present invention are free from any characteristics of exerting adverse effects on the ecosystem, for example, toxicity or teratogenicity, which obviously indicates that these compounds are highly useful as an antifouling agent causing no environmental pollution.

INDUSTRIAL APPLICABILITY

The antifouling agent of the present invention scarcely causes any problems in the hygienic safety and the environment (namely, having a low toxicity and a low persistence) and is capable of exerting its effects over a long period of time without adversely affecting the ecosystem or working environment.

We claim:

1. An antifouling agent containing at least one compound represented by the following general formula (I) as an active ingredient:

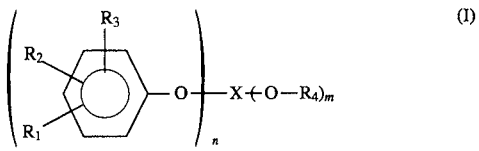

wherein $R_1$ is an alkyl group having 3 to 12 carbon atoms;

$R_2$ and $R_3$ independently represent each a hydrogen atom or an alkyl group having 3 to 12 atoms;

X represents P or

n is from 1 to 3;

m is from 0 to 2;

n+m is 3; and $R_4$ represents a hydrogen atom or an alkyl group having 1 to 30 carbon atoms.

2. An antifouling agent as claimed in claim 1 wherein said compound represented by the general formula (I) is a tris(alkylphenyl) phosphite.

3. An antifouling agent as claimed in claim 2 wherein said compound represented by the general formula (I) is tris(nonylphenyl) phosphite.

4. An antifouling agent as claimed in claim 1 wherein said compound represented by the general formula (I) is a tris(alkylphenyl) phosphate.

5. An antifouling agent as claimed in claim 4 wherein said compound represented by the general formula (I) is tris(nonylphenyl) phosphate.

* * * * *